United States Patent
Meridew (10) Patent No.: US 9,351,839 B2
(45) Date of Patent: May 31, 2016

(54) ACETABULAR CUP FIXATION

(71) Applicant: Biomet Manufacturing, LLC, Warsaw, IN (US)

(72) Inventor: Jason D. Meridew, Warsaw, IN (US)

(73) Assignee: BIOMET MANUFACTURING, LLC, Warsaw, IN (US)

(*) Notice: Subject to any disclaimer, the term of this patent is extended or adjusted under 35 U.S.C. 154(b) by 0 days.

(21) Appl. No.: 14/489,601

(22) Filed: Sep. 18, 2014

(65) Prior Publication Data

US 2015/0005892 A1    Jan. 1, 2015

Related U.S. Application Data

(62) Division of application No. 14/053,244, filed on Oct. 14, 2013, now abandoned, and a division of application No. 13/299,663, filed on Nov. 18, 2011, now Pat. No. 8,556,985, and a division of application No. 12/370,951, filed on Feb. 13, 2009, now abandoned.

(60) Provisional application No. 61/030,027, filed on Feb. 20, 2008.

(51) Int. Cl.
| | |
|---|---|
| A61F 2/32 | (2006.01) |
| A61F 2/34 | (2006.01) |
| A61B 17/80 | (2006.01) |
| A61B 17/86 | (2006.01) |
| A61F 2/30 | (2006.01) |

(52) U.S. Cl.
CPC .............. *A61F 2/34* (2013.01); *A61B 17/8042* (2013.01); *A61B 17/8047* (2013.01); *A61B 17/8052* (2013.01); *A61B 17/8057* (2013.01); *A61B 17/8685* (2013.01); *A61F 2002/30332* (2013.01); *A61F 2002/30378* (2013.01); *A61F 2002/30485* (2013.01); *A61F 2002/30538* (2013.01); *A61F 2002/3401* (2013.01); *A61F 2002/3404* (2013.01); *A61F 2002/3446* (2013.01); *A61F 2220/0025* (2013.01); *A61F 2220/0033* (2013.01); *A61F 2250/0006* (2013.01)

(58) Field of Classification Search
CPC .............. A61F 2/34; A61F 2002/3401; A61F 2002/3403; A61F 2002/3404; A61B 17/8047; A61B 17/8052
See application file for complete search history.

(56) References Cited

U.S. PATENT DOCUMENTS

| | | |
|---|---|---|
| 3,641,590 A | 2/1972 | Michele |
| 3,685,058 A | 8/1972 | Tronzo |
| 4,062,891 A | 12/1977 | Remy |
| 4,563,778 A | 1/1986 | Roche et al. |
| 4,792,337 A | 12/1988 | Muller |
| 4,792,339 A | 12/1988 | Tepic |
| 4,795,469 A | 1/1989 | Oh |

(Continued)

*Primary Examiner* — Brian Dukert
(74) *Attorney, Agent, or Firm* — Schwegman Lundberg & Woessner, P.A.

(57) ABSTRACT

An acetabular cup system includes an acetabular cup having a wall with an inner surface and an outer surface. The acetabular cup includes a fixation opening through the wall, the fixation opening including a first wall portion adjacent to the inner surface and a second wall portion adjacent to the outer surface. The acetabular cup system also includes a fixation fastener including a head and a shaft with a bone-anchoring portion. The fastener can be inserted though the fixation opening. The head includes a first head portion engageable with the first wall portion and a second head portion engageable with the second wall portion.

19 Claims, 9 Drawing Sheets

(56) References Cited

U.S. PATENT DOCUMENTS

| | | |
|---|---|---|
| 4,813,961 A | 3/1989 | Sostegni |
| 4,822,367 A | 4/1989 | Stuhmer |
| 4,828,565 A | 5/1989 | Duthoit et al. |
| 4,840,632 A | 6/1989 | Kampner |
| 4,871,368 A | 10/1989 | Wagner |
| 4,955,825 A | 9/1990 | Groth et al. |
| 5,004,476 A | 4/1991 | Cook |
| 5,021,062 A | 6/1991 | Adrey et al. |
| 5,290,281 A | 3/1994 | Tschakaloff |
| 5,310,408 A | 5/1994 | Schryver et al. |
| 5,360,452 A | 11/1994 | Engelhardt et al. |
| 5,534,032 A | 7/1996 | Hodorek |
| 5,590,281 A | 12/1996 | Stevens |
| 5,601,553 A | 2/1997 | Trebing et al. |
| 5,607,427 A | 3/1997 | Tschakaloff |
| 5,709,686 A | 1/1998 | Talos et al. |
| 5,888,204 A | 3/1999 | Ralph et al. |
| 5,954,722 A | 9/1999 | Bono |
| 5,961,524 A | 10/1999 | Crombie |
| 6,004,323 A | 12/1999 | Park et al. |
| 6,206,881 B1 | 3/2001 | Frigg et al. |
| 6,322,562 B1 | 11/2001 | Wolter |
| 6,454,769 B2 * | 9/2002 | Wagner et al. ................ 606/279 |
| 6,605,090 B1 | 8/2003 | Trieu et al. |
| 6,679,883 B2 | 1/2004 | Hawkes et al. |
| 6,695,845 B2 | 2/2004 | Dixon et al. |
| 7,172,593 B2 | 2/2007 | Trieu et al. |
| 7,195,633 B2 | 3/2007 | Medoff et al. |
| 7,635,447 B2 | 12/2009 | Hamman et al. |
| 7,780,711 B2 | 8/2010 | Orbay et al. |
| 8,556,985 B2 | 10/2013 | Meridew |
| 2004/0260291 A1 | 12/2004 | Jensen |
| 2006/0116678 A1 | 6/2006 | Impellizzeri |
| 2006/0235400 A1 | 10/2006 | Schneider |
| 2006/0241781 A1 | 10/2006 | Brown et al. |
| 2007/0055249 A1 | 3/2007 | Jensen et al. |
| 2007/0162147 A1 * | 7/2007 | Lewis et al. ................ 623/22.21 |
| 2009/0210067 A1 | 8/2009 | Meridew |
| 2014/0058525 A1 | 2/2014 | Meridew |

* cited by examiner

ACETABULAR CUP FIXATION

CROSS-REFERENCE TO RELATED APPLICATIONS

This application is a divisional of U.S. patent application Ser. No. 14/053,244, filed on Oct. 14, 2013; which is a divisional of U.S. patent application Ser. No. 13/299,663, filed on Nov. 18, 2011 (now U.S. Pat. No. 8,556,985); which is a divisional of U.S. patent application Ser. No. 12/370,951, filed on Feb. 13, 2009; which claims the benefit of U.S. Provisional Application No. 61/030,027, filed on Feb. 20, 2008. The entire disclosures of the above applications are incorporated herein by reference.

INTRODUCTION

Acetabular cups are used with various fixation fasteners that can secure the cups to the bone in orthopedic procedures.

The present teachings provide various methods and devices for securing acetabular cups to bone with locking fixation fasteners.

SUMMARY

The present teachings provide various acetabular cup systems and methods of locking fixation fasteners to acetabular cups and preventing loosening and back out of the fixation fasteners during use.

The present teachings provide an acetabular cup system that includes an acetabular cup having a wall with an inner surface and an outer surface. The acetabular cup includes a fixation opening through the wall, the fixation opening including a first wall portion adjacent to the inner surface and a second wall portion adjacent to the outer surface. The acetabular cup system also includes a fixation fastener including a head and a shaft with a bone-anchoring portion. The fastener can be inserted though the fixation opening. The head includes a first head portion engageable with the first wall portion and a second head portion engageable with the second wall portion.

In another aspect, the acetabular cup system includes an acetabular cup having a wall with an inner surface and an outer surface, the acetabular cup including a fixation opening through the wall, the fixation opening including a first wall portion adjacent to the inner surface and a second wall portion adjacent to the outer surface, the first wall portion being internally threaded and the second wall portion being unthreaded and tapered. The acetabular cup system also includes a fixation fastener including a head and a shaft with a bone anchoring portion, the fastener insertable though the fixation opening, the head including a first head portion threadably engageable with the first wall portion and a second head portion tapered for taper lock connection with the second wall portion.

In another aspect, the acetabular cup system includes an acetabular cup having a wall with an inner surface and an outer surface, the acetabular cup including a fixation opening through the wall, the fixation opening having an unthreaded surface, and a fixation fastener including a head and a shaft with a bone anchoring portion, the fastener insertable though the fixation opening, the head including a threaded portion with self-tapping threads threadably engageable with the fixation opening.

In a further aspect, the acetabular cup system includes an acetabular cup having a wall with an inner surface and an outer surface, the acetabular cup including a fixation opening through the wall, the fixation opening having a threaded portion, and a fixation fastener including an inner head attached to a bone-anchoring shaft and an outer head pivotably coupled to the inner head, the outer head including a threaded portion threadably engageable with the fixation opening, the inner head including a driver engagement recess.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although the present teachings illustrate various fasteners for use with acetabular cups, the present teachings can be used for fixation of fasteners to other prosthetic components.

The present teachings provide various aspects related to the fixation of acetabular cups to bone through the use of fixation fasteners and preventing loosening or back out of the fasteners during use. Any type of acetabular cups can be used, including, but not limited to, porous metal acetabular cups, such as porous titanium cups, and the Regenerex™ cup, commercially available from Biomet, Inc., of Warsaw, Ind. Methods for fabricating acetabular cups and other implant components from porous metal material are described in co-pending and commonly assigned patent application Ser. No. 11/357,929, filed Feb. 17, 2006 (now U.S. Pat. No. 7,635,447, Issued Dec. 22, 2009), the disclosure of which is incorporated by reference herein.

Referring to FIGS. 1-10, an exemplary acetabular cup 100 can include a wall 109 having a concave inner surface 101 and a convex outer surface 107. The wall 109 can include one or more fixation holes or other through openings 102 for receiving corresponding fixation fasteners 200. An exemplary fixation fastener 200 can generally include a head 202 and a shaft or shank 204 with a threaded portion 208 for anchoring into the acetabular bone.

Figure 1:
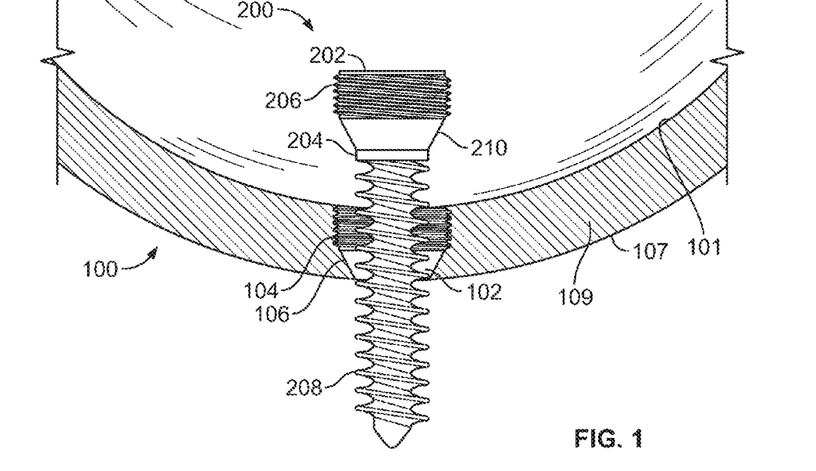
FIG. 1 is a sectional elevation view of an acetabular cup and a fixation fastener according to the present teachings.
Figure 2:
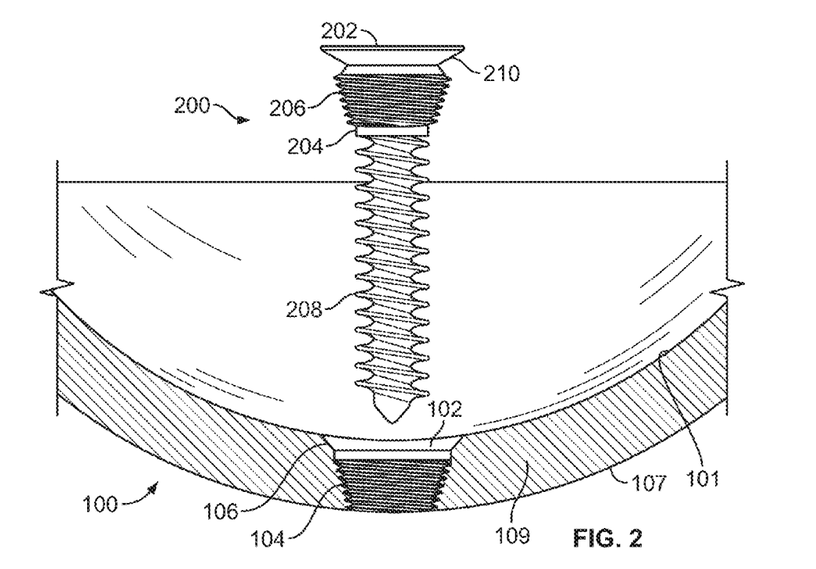
FIG. 2 is a sectional elevation view of an acetabular cup and a fixation fastener according to the present teachings.

Referring to FIGS. 1 and 2, the head 202 of the fastener 200 can include a male threaded portion 206 and a male tapered portion 210. The tapered portion 210 of the head 202 can taper toward the shank 204 of the fastener 200. The fixation opening 102 of the cup 100 can similarly have a female threaded portion 104 and a female tapered portion 106. The tapered portion 210 of the head 202 of the fastener 200 and the tapered portion 106 in the opening 102 of the acetabular cup 100 can have appropriate taper angles to form a taper lock connection. Accordingly, as the threaded portion 206 of the head 202 engages the threaded portion 104 of the opening 102 of the cup 100, the tapered portion 210 of the head 202 of the fastener 200 can mate and taper lock with the tapered portion 106 of the opening 102, locking the fastener 200 to the cup 100.

In the exemplary illustration of FIG. 1, the tapered portion of the head 202 is adjacent to the shank 204, and the tapered portion 106 of the cup 100 is adjacent the outer convex surface of the cup 100. In the exemplary illustration of FIG. 2, the positions of the tapered and threaded portions are reversed. Specifically, the threaded portion 206 of the head 202 is adjacent the shank 204 and the threaded portion 104 of the opening 102 is adjacent the outer convex surface of the cup 100. Referring to FIG. 2, the threaded portion 206 of the head 202 and the threaded portion 104 of the opening 102 can be tapered, as shown in FIG. 2, or straight, similarly to FIG. 1.

Figure 3:
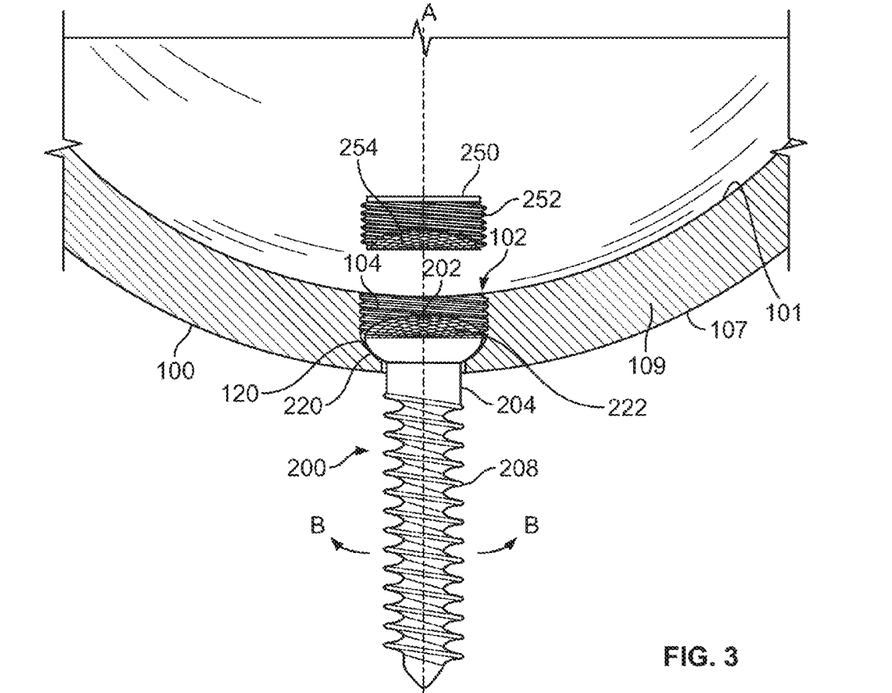
FIG. 3 is a sectional elevation view of an acetabular cup, a fixation fastener and a locking cap according to the present teachings.

Referring to FIG. 3, the head 202 of the fastener 200 can include a curved or rounded or spherical undersurface 220 and a rounded upper surface 222 that can be textured. In addition, the opening 102 in the acetabular cup 100 can have a similarly curved or rounded or spherical lower portion 120 configured to receive the undersurface 220 of the head 202 of fastener 200 adjustably, such that the fastener 200 can angulate or pivot in the direction of the curved arrows B relative to an axis A passing through the center of the opening 102. The opening 102 of the acetabular cup 100 can include a threaded portion 104 above the spherical portion 120. The threaded portion 104 of the opening 102 can engage the external threads 252 of a threaded washer or other locking cap or locking member 250. The threaded washer 250 can include a textured undersurface 254 that can engage the textured upper surface 222 of the head 202 of the fastener 200. In operation, the fastener 200 can be positioned within the opening 102 of the acetabular cup 100, adjustably angled relative to the axis A of the opening 102 and threaded into the bone. Once the fastener 200 is anchored into the bone, the threaded washer 250 can be inserted into the opening 102 and rotated such that the undersurface 254 of the threaded washer 250 engages the upper surface 222 of the head 202 of the fastener 200, thereby locking the fastener 200 in the acetabular cup 100 and the bone and preventing back out of the fastener 200 during use.

Figure 4:
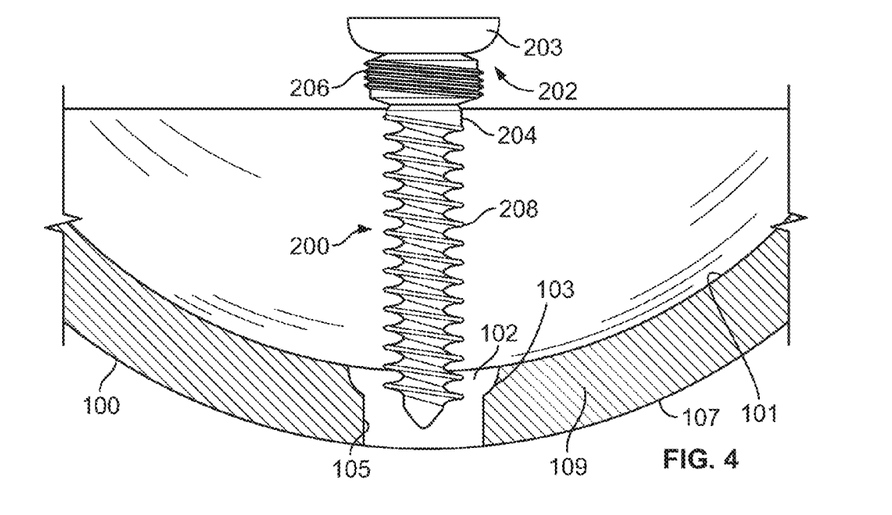
FIG. 4 is a sectional elevation view of an acetabular cup and a fixation fastener according to the present teachings.

Referring to FIG. 4, the head 202 of the fastener 200 can include a curved or spherical portion 203 and a threaded portion 206, which can be cylindrical. The threads of the threaded portion 206 can be self tapping. The opening 102 in the acetabular cup 100 can include a corresponding spherical portion 103 that can engage the spherical portion 203 of the head 202 of the fastener 200. The opening 102 in the acetabular cup 100 can also include a cylindrical portion 105. During insertion, the self-tapping threaded portion 206 on the head 202 of the fastener 200 can tap threads into the wall of the cylindrical portion 105 of the opening 102, until the head 202 of the fastener 200 is fully seated in the opening 102 and secured to the cup 100. In this respect, the acetabular cup 100 can be made of porous metal, such as porous titanium, Regenerex™, or other biocompatible material that can be relatively easily tapped.

Figure 5:
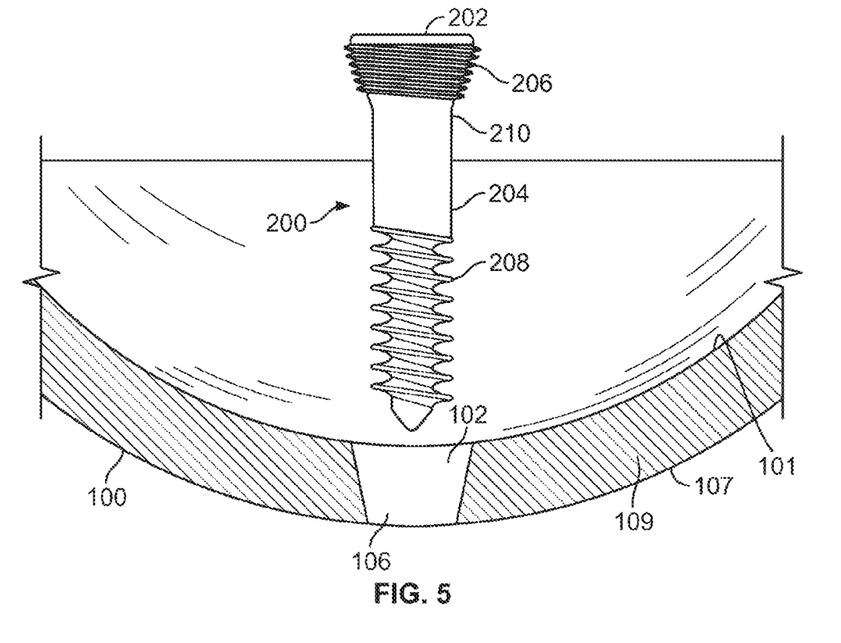
FIG. 5 is a sectional elevation view of an acetabular cup and a fixation fastener according to the present teachings.

Referring to FIG. 5, the head 202 of the fastener 200 can include a tapered threaded portion 206 with self-tapping threads which can cut into the similarly tapered opening 102 of the acetabular cup 100. The acetabular cup 100 can be made of porous metal for tapping by the self-tapping threaded portion 206 of the head 202 of the fastener 200, as discussed above in connection with FIG. 4.

Figure 6:
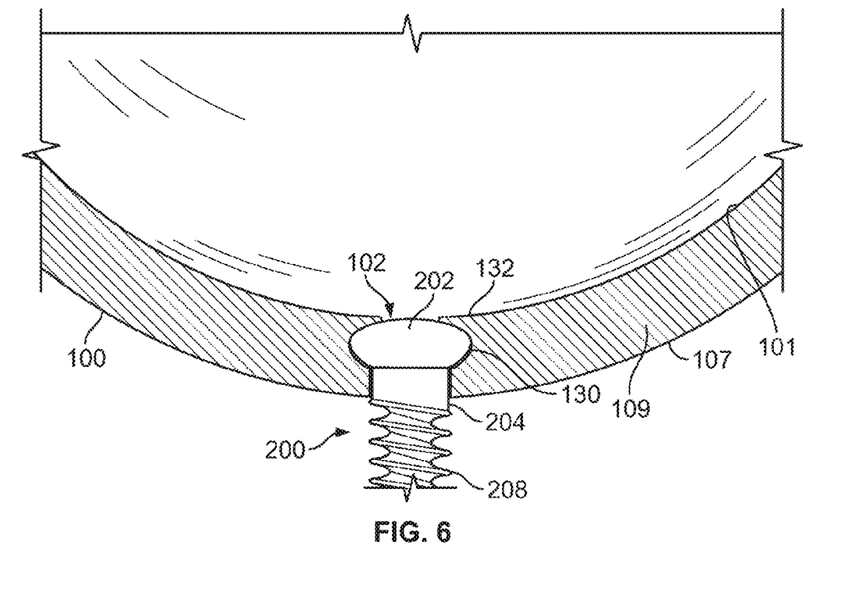
FIG. 6 is a sectional elevation view of an acetabular cup and a fixation fastener according to the present teachings.

Referring to FIG. 6, the acetabular cup 100 can be made of porous metal that can be peened or otherwise plastically deformed. The head 202 of the fastener 200 is inserted through the opening 102 and positioned on a pocket or seat 130 defined by the opening 102. An area 132 of the acetabular cup 100 immediately surrounding the upper portion of the opening 102 adjacent to the head 202 of the fastener 200 can be peened or otherwise deformed with a tool such that the deformed area 132 can overlap a portion of the head 202 and trap the head 202 in the seat 130 preventing the fastener 200 from backing out of the opening 102 during use.

Figure 7:
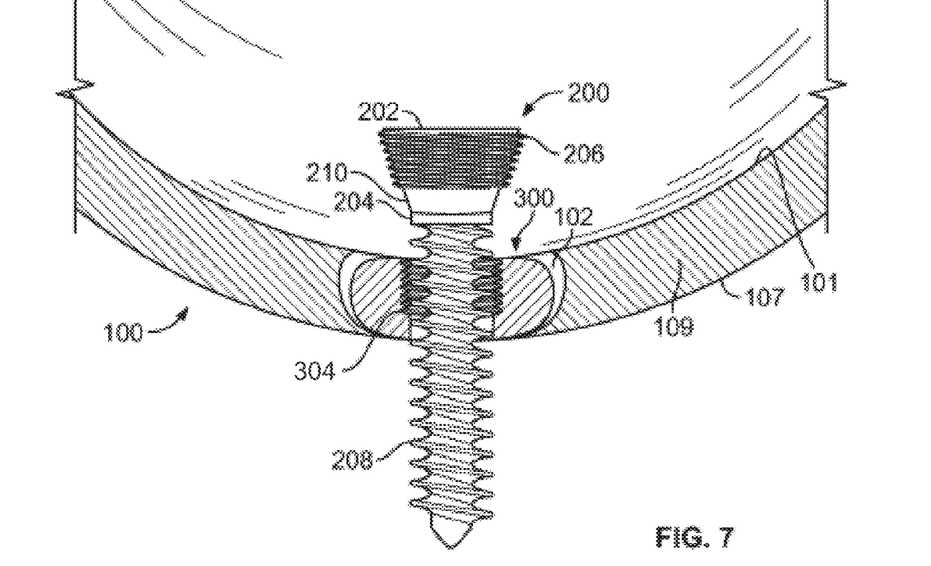
FIG. 7 is a sectional elevation view of an acetabular cup, a fixation fastener and an insert according to the present teachings.
Figure 7A:
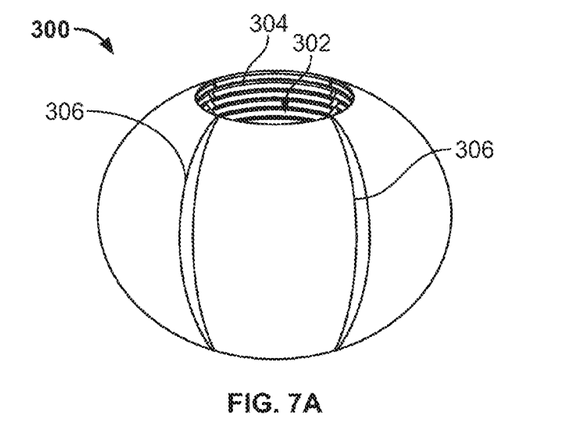
FIG. 7A is a perspective view of the insert of FIG. 7.

Referring to FIGS. 7 and 7A, the opening 102 of the cup 100 can be spherically shaped and rotatably receive a spherically shaped insert 300. The insert 300 can include a through bore 302 having internal threads 304. The insert 300 can include meridian slits 306 that allow expansion of the insert 300. The head 202 of the fastener 200 can include a tapered portion 210, which can be fully or partially threaded with threads 206. The fastener 200 can be inserted through the bore 302, and the head 202 of the fastener 200 can be threadably engaged with the threads 304 of the insert 300, forcing the insert 300 to expand. The expansion of the insert 300 lockingly engages the insert 300 to the opening 102 of the acetabular cup 100 and prevents rotational movement between the insert 300 and the acetabular cup 100. Before the fastener 200 is inserted, the insert 300 can move in a limited manner with respect to the acetabular cup 100 so as to permit optimal positioning of the fastener 200 with respect to the cup 100 before securing the fastener 200 to the cup 100.

Figure 8:
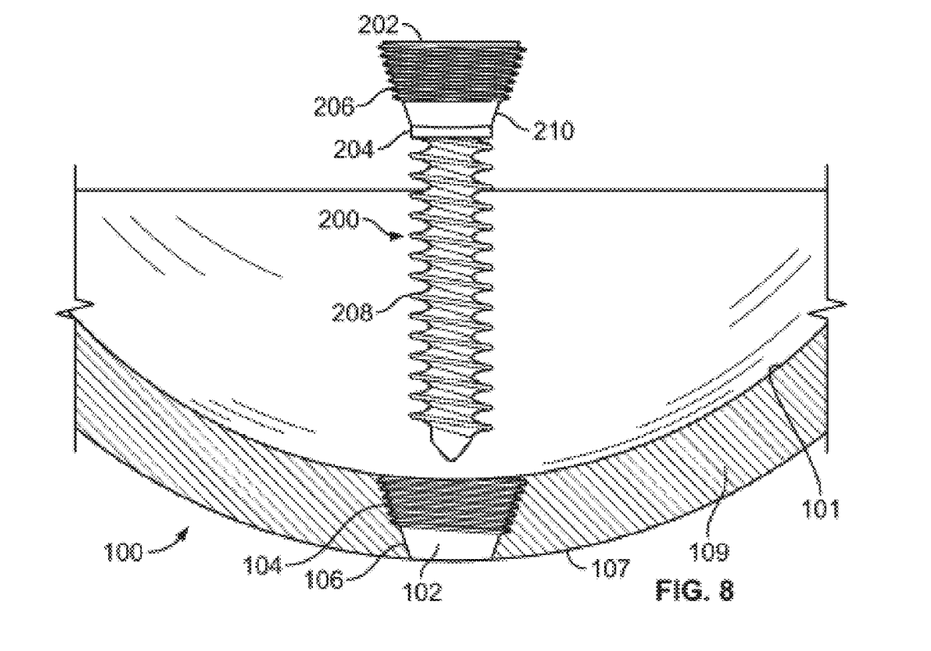
FIG. 8 is a sectional elevation view of an acetabular cup and a fixation fastener according to the present teachings.

Referring to FIG. 8, the opening 102 in the acetabular cup 100 can include a fully threaded portion 104 engaging a corresponding threaded portion 206 of the head 202 of the fastener 200. The opening 102 and the head 202 can be straight or tapered and can be fully threaded or have respective unthreaded portions 106 and 210.

Figure 9:
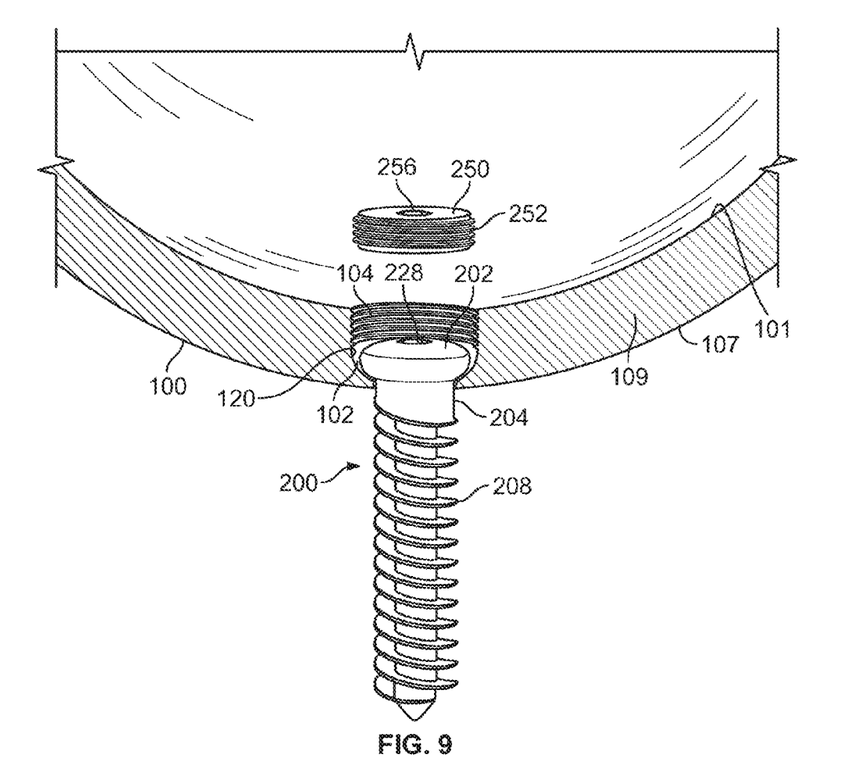
FIG. 9 is a sectional elevation view of an acetabular cup, a fixation fastener and a locking cap according to the present teachings.

Referring to FIG. 9, the fixation fastener 200 can include a spherical head 202 with a hex or otherwise shaped recess 228 in its upper surface to allow the fastener 200 to be rotated by an appropriate driver. The opening 102 of the acetabular cup 100 can include an upper internally threaded portion 104 and a lower spherical portion defining a seat 120. The fastener 200 can be inserted into the opening 102 of the acetabular cup 100 such that the head 202 of the fastener 200 is received in the seat 120 of the acetabular cup 100. A locking nut 250 having external threads 252 and a recess 256 for a driver can be threadably engaged with the threaded portion 104 of the opening 102, thereby locking the head 202 of the fastener 200 to the acetabular cup 100.

Figure 10:
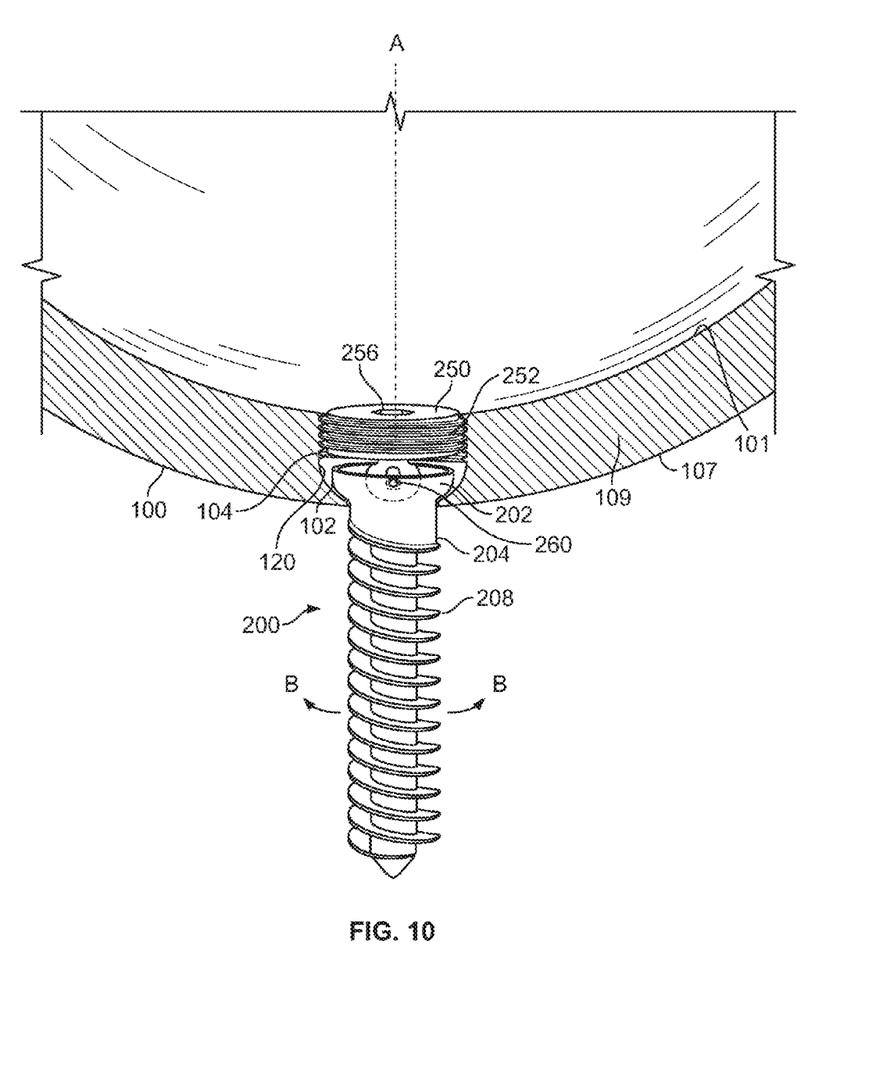
FIG. 10 is a sectional elevation view of an acetabular cup, and a two-piece fixation fastener according to the present teachings.

Referring to FIG. 10, the opening 102 of the acetabular cup 100 is similar to the opening 102 shown in FIG. 9. The fastener 200 can include a head 202 in the form of a spherical cavity. A locking washer 250 can be pivotably coupled to the head 202 of the fastener 202 with a pivot pin 260 forming a two-piece fixation construct. The pivot pin 260 allows the shank 204 of the fastener 200 to angulate relative to the washer 250 such that the shank 204 can be inserted at various angles relative to the axis A of the opening 102, while maintaining the ability to prevent back out by threadably engaging the locking washer 250 to the internal threaded portion 104 of the opening 102 of the acetabular cup 100.

Figure 11:
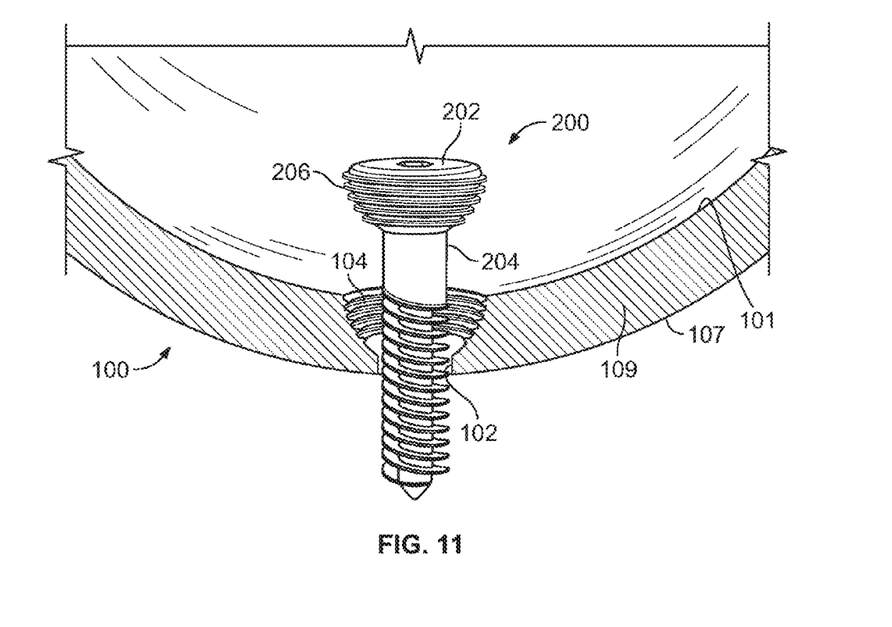
FIG. 11 is a sectional elevation view of an acetabular cup and a fixation fastener according to the present teachings.

Referring to FIG. 11, the fixation fastener 200 can include at least a spherical head portion or, alternatively, a spherical head 202 having an external threaded portion 206. The threaded head 202 of the fastener can be received in a threaded spherical socket 104 defined in the opening 102 of the acetabular cup 100. Further, the threaded head 202 of the fastener can be rotated and inserted at an angle not aligned with the axis of the opening 102, such that the threads of the head 202 of the fastener 200 and the threads of the opening 102 of the acetabular cup 100 can cross-thread and lock.

Figure 12:
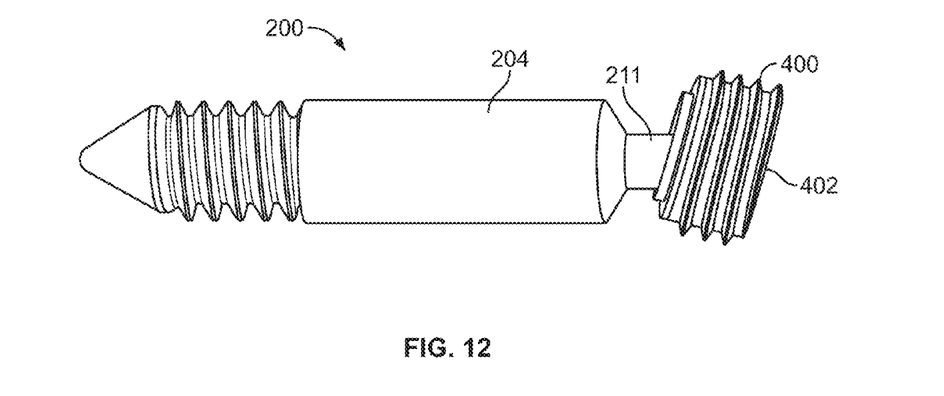
FIG. 12 is a perspective view of a variable angle locking fixation fastener according to the present teachings.
Figure 12A:
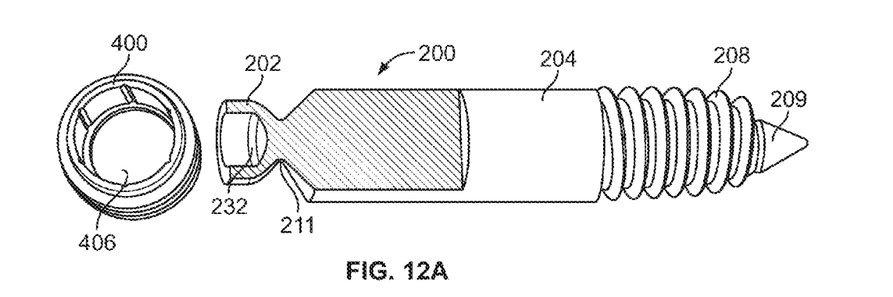
FIG. 12A is an exploded and partially sectional view of the fixation fastener of FIG. 12.
Figure 12B:
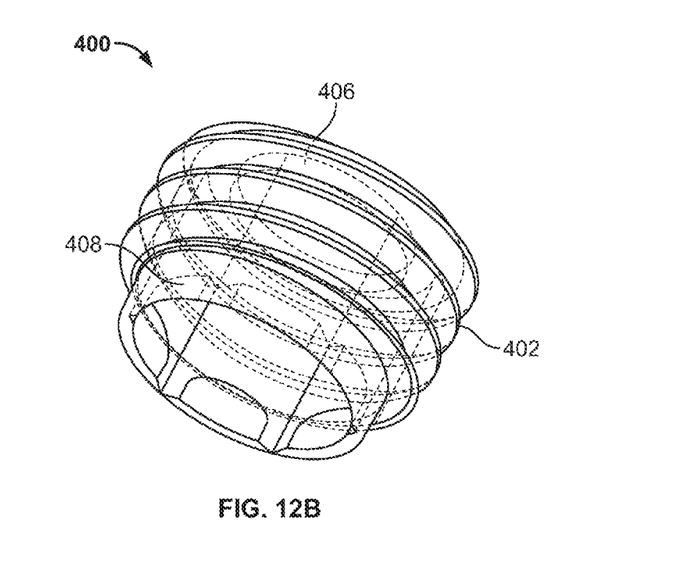
FIG. 12B is a perspective view of the outer head of the fixation fastener of FIG. 12.
Figure 12C:
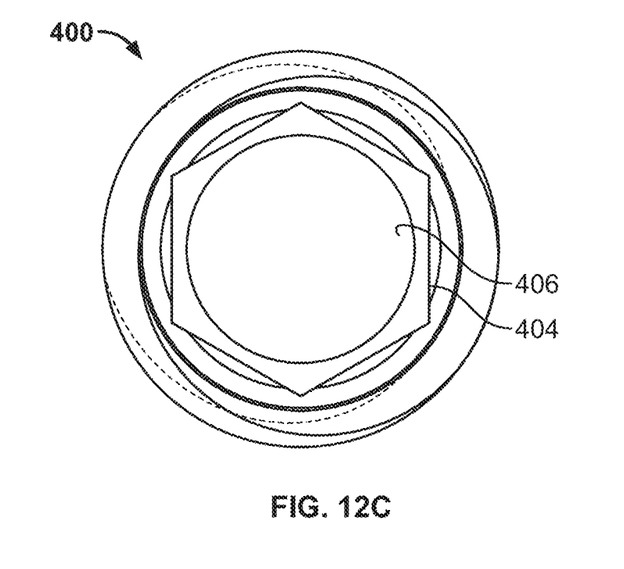
FIG. 12C is a plan view of the outer head of FIG. 12B.
Figure 12D:
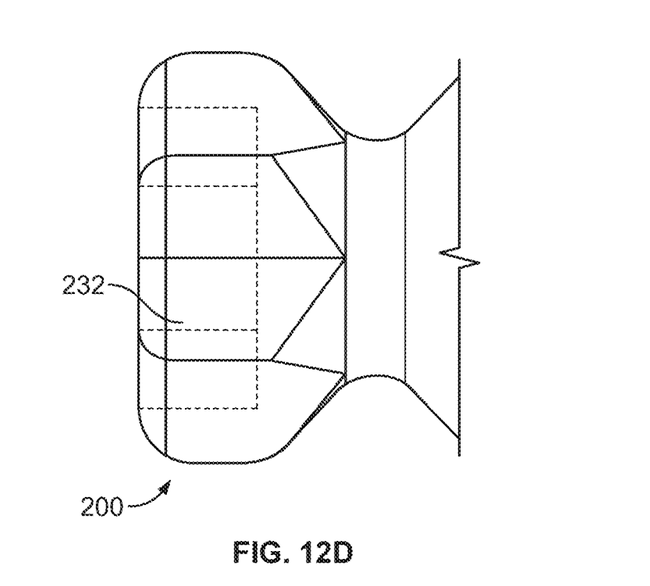
FIG. 12D is a side view detail of the fixation fastener of FIG. 12, showing the inner head of the fixation fastener.

Referring to FIGS. 12-12D, various aspects of a variable angle locking fastener 200 are illustrated. The fastener 200 can include an inner head 202 fixedly connected to a shank 204 with a neck portion 211, and an outer head 400 pivotably coupled with the inner head 202. The inner head 202 can include a driver engaging recess 232. The shank 204 can include a threaded portion 208 and an anchoring distal tip 209. The inner head 202 can be pivotably received in an opening 406 of the outer head 400. The outer head 400 can include outer threads 402 for threadably locking the fixation fastener 200 into a threaded opening of an acetabular cup or other implant. The outer head 400 can include a driver engagement feature 404 and an end lip 408 that can be swaged or otherwise deformed to capture the inner head 202. The threaded outer head 400 can lock the fixation fastener 200 into a similarly threaded hole of an acetabular cup 100, or a fixation plate or other implant, preventing back out of the fixation fastener 200, while allowing angulation of the shank 204 for anchoring the fixation fastener 200 at a selected orientation.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings that various changes, modifications and variations can be made therein without departing from the spirit and scope of the present teachings.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A locking system, comprising:
an acetabular cup having a wall with an inner surface and an outer surface, the acetabular cup including a fixation opening with a curved surface through the wall;
an insert configured to be received in the fixation opening, the insert includes a through bore and a plurality of expansion members disposed at an outer surface of the insert, the through bore including a first wall portion configured to be positioned adjacent to the inner surface and a second wall portion configured to be positioned adjacent to the outer surface, wherein the first wall portion is internally threaded and the second wall portion is unthreaded; and
a fixation fastener including a head and a shaft with a bone-anchoring portion, the fastener insertable through the through bore, the head including a first head portion engageable with the first wall portion and a second head portion engageable with the second wall portion.

2. The locking system of claim 1, wherein the first head portion is externally threaded.

3. The locking system of claim 2, wherein the second head portion is unthreaded and tapered and the second wall portion is tapered and configured to form a taper lock connection with the second head portion, and wherein the first head portion is contiguous to the second head portion.

4. The locking system of claim 3, wherein the first head portion is cylindrical and the first wall portion is cylindrical.

5. The locking system of claim 3, wherein the first head portion is tapered and the first wall portion is tapered.

6. The locking system of claim 3, wherein unthreaded second head portion is between the first head portion and the shaft.

7. The locking system of claim 1, wherein the curved surface of the fixation opening is substantially spherical.

8. The locking system of claim 1, wherein the insert is substantially spherical.

9. The locking system of claim 1, wherein the insert includes meridian slits to form the expansion members;
   wherein the expansion members are configured to be disposed adjacent to an inner surface of the curved fixation opening.

10. The locking system of claim 9, wherein the expansion members expand in response to the fixation fastener being inserted into the through bore, wherein the expansion members are moved by the fixation fastener to lock the insert against the curved surface of the fixation opening.

11. The locking system of claim 1, wherein the head is threaded and configured to be received by a threaded portion of the insert and the shaft is cylindrical and threaded with self-tapping threads.

12. A method of locking a system, comprising:
   positioning an insert in a fixation opening of an acetabular cup, wherein the acetabular cup has a wall with an inner surface and an outer surface, wherein the fixation opening has a curved surface formed through the wall, wherein the insert has a through bore passing through the insert, wherein the insert has a plurality of expansion members disposed at an outer surface of the insert, wherein the through bore has a first wall portion adjacent to the inner surface and a second wall portion adjacent to the outer surface, wherein the first wall portion is internally threaded and the second wall portion is unthreaded; and
   passing a fixation fastener through the through bore of the provided insert, the fixation fastener provided with a head and a shaft with a bone-anchoring portion, the head provided with a first head portion engageable with the first wall portion and a second head portion engageable with the second wall portion.

13. The method of claim 12, further comprising:
   engaging external threads on the first head portion with the first wall portion.

14. The method of claim 13, further comprising:
   forming a taper lock connection between the second head portion and the second wall portion.

15. The method of claim 14, further comprising:
   engaging a tapered portion of the first head portion and a tapered portion of the first wall portion.

16. The method of claim 12, further comprising:
   providing the insert to be substantially spherical.

17. A locking system, comprising:
   a prosthesis having:
      a curved wall extending from an apical region to a rim, wherein the curved wall has an inner surface and an outer surface,
      a fixation opening formed by a fixation surface that extends through the wall between the inner surface and the outer surface;
   an expandable insert configured to be received in the fixation opening, the insert having a first wall portion, a second wall portion separate from the first wall portion, and a through bore; and
   a fixation fastener including a head and a shaft with a bone-anchoring portion, wherein at least a portion of the head tapers from a broad portion to a narrow portion, wherein the broad portion is externally threaded and the narrow portion is unthreaded, wherein the broad portion of the head is engageable with the first wall portion of the insert and the narrow portion of the head is engageable with the second wall onion of the insert;
   wherein the fixation fastener is configured to be inserted through the through bore to expand the insert to lock the broad portion and the narrow portion of the fixation fastener within the fixation opening.

18. The locking system of claim 17, wherein the insert comprises:
   meridian slits that allow expansion of the insert.

19. The locking system of claim 17, wherein the fixation surface is curved between the inner surface and the outer surface;
   wherein an outer surface of the insert is curved.

\* \* \* \* \*